US010309965B2

(12) United States Patent
Bedin et al.

(10) Patent No.: US 10,309,965 B2
(45) Date of Patent: Jun. 4, 2019

(54) METHOD AND KIT FOR DETERMINING THE PROBABILITY THAT A PATIENT WILL DEVELOP A SEVERE CASE OF DENGUE

(71) Applicant: BIOMERIEUX, Marcy L'Etoile (FR)

(72) Inventors: Frédéric Bedin, Lyons (FR); Romain Fragnoud, Juvisy sur Orge (FR)

(73) Assignee: BIOMERIEUX, Marcy L'Etoile (FR)

( * ) Notice: Subject to any disclaimer, the term of this patent is extended or adjusted under 35 U.S.C. 154(b) by 0 days.

(21) Appl. No.: 15/912,730

(22) Filed: Mar. 6, 2018

(65) Prior Publication Data

US 2018/0196046 A1  Jul. 12, 2018

Related U.S. Application Data

(62) Division of application No. 15/117,765, filed as application No. PCT/FR2015/050352 on Feb. 12, 2015, now Pat. No. 9,945,857.

(30) Foreign Application Priority Data

Feb. 18, 2014  (FR) ..................................... 14 51274

(51) Int. Cl.
*A61K 39/00* (2006.01)
*A61K 39/395* (2006.01)
*C07K 16/18* (2006.01)
*C07K 16/28* (2006.01)
*C07K 16/44* (2006.01)
*G01N 33/569* (2006.01)

(52) U.S. Cl.
CPC . *G01N 33/56983* (2013.01); *G01N 2333/185* (2013.01); *G01N 2333/521* (2013.01); *G01N 2800/50* (2013.01); *G01N 2800/52* (2013.01); *Y02A 50/53* (2018.01)

(58) Field of Classification Search
CPC ......... G01N 2333/185; G01N 2800/52; G01N 33/56983; G01N 2333/521; Y02A 50/53
See application file for complete search history.

(56) References Cited

U.S. PATENT DOCUMENTS

2010/0068147 A1  3/2010  Hibberd et al.

FOREIGN PATENT DOCUMENTS

WO  2013/110894 A1  8/2013
WO  2013/148335 A1  10/2013

OTHER PUBLICATIONS

S.P. Ong et al., "Identifying Host Factors Involved in Mediating Vascular Permeability During Dengue Virus Infection," National University of Singapore, 13th International Congress on Infectious Diseases Abstracts, Poster Presentations, 2008, p. e297.
Clyde et al., "Recent Advances in Deciphering Viral and Host Determinants of Dengue Virus Replication and Pathogenesis," Journal of Virology, Dec. 2006, p. 11418-11431.
Srichaikul et al., "Platelet Function During the Acute Phase of Dengue Hemorrhagic Fever," Southeast Asian Journal of Tropical Medicine and Public Health, vol. 20, No. 1, Mar. 1989, pp. 19-25.
Scott B. Halstead, "Dengue," The Lancet, vol. 370, Nov. 10, 2007, pp. 1644-1652.
Romain Drissi, et al., "Proteomics Methods for Subcellular Proteome Analysis," FEBS Journal 280, 2013, pp. 5626-5634.
A.S. Leong et al., "The Pathology of Dengue Hemorrhagic Fever," Seminars in Diagnostic Pathology, vol. 24, No. 4, Nov. 2007, pp. 227-236.
Luis Angel Villar-Centeno et al., "Biochemical Alterations as Markers of Dengue Hemorrhagic Fever," The American Society of Tropical Medicine and Hygiene, 2008, pp. 370-374.
Hellen Dassen, et al., "Olfactomedin-4 Regulation by Estrogen in the Human Endometrium Requires Epidermal Growth Factor Signaling," Metabolic, Endocrine and Genitourinary Pathology, The American Journal of Pathology, vol. 177, No. 5, Nov. 2010, pp. 2495-2508.
Manabu Maeda et al., "Plasma Levels of Molecular Markers of Blood Coagulation and Fibrinolysis in Progressive Systemic Sclerosis (PSS)," Journal of Dermatological Science, 1996, pp. 223-227.
U.S. Appl. No. 15/117,977, filed Aug. 10, 2016.
May 6, 2015 International Search Report issued in PCT Application No. PCT/FR2015/050352.
May 12, 2015 International Search Report issued in PCT Application No. PCT/FR2015/050353.
Aug. 27, 2015 Written Opinion issued in PCT Application No. PCT/FR2015/050352.
Aug. 27, 2015 Written Opinion issued in PCT Application No. PCT/FR2015/050353.
May 31, 2017 Office Action issued in U.S. Appl. No. 15/117,977.

*Primary Examiner* — Barry A Chestnut
(74) *Attorney, Agent, or Firm* — Oliff PLC

(57) ABSTRACT

A kit for determining whether a patient will develop severe dengue includes a binding partner for platelet factor 4 and a binding partner for at least one member selected from the group consisting of dengue virus NS1 protein, olfactomedin 4, and α2-macroglobulin. The kit may further include a label reagent capable of generating a detectable signal.

9 Claims, 3 Drawing Sheets

METHOD AND KIT FOR DETERMINING THE PROBABILITY THAT A PATIENT WILL DEVELOP A SEVERE CASE OF DENGUE

This is a Division of application Ser. No. 15/117,765 filed Aug. 10, 2016, which is a National Stage Entry of PCT/FR2015/050352 filed Feb. 12, 2015, which claims priority to FR 1451274 filed Feb. 18, 2014. The disclosures of the prior applications are hereby incorporated by reference herein in their entireties.

The subject of the present invention is a method for the early prediction of severe dengue or hemorrhagic dengue using protein markers.

Over the past 30 years, dengue, a viral disease transmitted by urban hematophagous mosquitoes of the *Aedes* genus has worryingly spread throughout the world. It is currently a real public health problem for more than one hundred countries located in the subtropical zone, particularly in the Pacific West, South America and South-East Asia zones. The emergence of the disease is largely due to the population explosion and to chaotic urbanization. Climatic abnormalities also play a not insignificant role.

In this respect, dengue could emerge in the western regions of the world which until now have been spared the virus. Thus, *Aedes albopictus*, one of the vectors of the disease, has recently been found in the North of Italy and in the South of France. Most recently, autochthonous cases of dengue have been recorded in the South of France. It is estimated that close to three billion people are exposed to the risks of dengue. Close to one million hospitalizations are registered yearly and there have been thousands of deaths. Children are the main victims of the disease.

The dengue virus is a single-stranded, positive-polarity enveloped RNA virus of the family Flaviviridae. The genome of the virus (11 000 nucleotides) encodes a polyprotein of approximately 3400 amino acids which undergoes co- and post-translational cleavage which results in structural proteins (C, prM, E) and non-structural proteins (NS1, NS2A, NS2B, NS3, NS4A, NS4B, NS5). There are 4 viral serotypes (DV1 to DV4), which can coexist in endemic zones. There is approximately 70% sequence homology between the various serotypes. Infection by a given serotype confers long-term immunity for this serotype. Cross-protection lasts only a few months: reinfection is therefore possible with a different serotype.

Infection begins with a bite from a mosquito infected with one of the dengue viruses. Incubation, the period during which the virus replicates in the blood without however giving rise to any symptoms, generally lasts from 4 to 10 days. The first signs occur after the incubation period.

In its conventional form ("conventional" dengue fever: DF), dengue is characterized by sudden-onset hyperthermia accompanied by one or more of the following symptoms: shivering, headaches, joint and/or muscle pain, nausea and vomiting. A rash may also appear, generally on around the 5th day of symptoms. This acute febrile stage, which corresponds to the viremic phase, generally lasts from 3 to 5 days (extremes: 2 to 7 days). More than 95% of cases will have no signs of severe illness and will recover with no complications in under 7 days.

In 2 to 4% of cases, the patient may develop a critical phase characterized by a more or less severe plasma leakage syndrome and an increased hematocrit level, leading to dengue hemorrhagic fever: DHF. This phase typically (but not necessarily) appears at the time of defervescence, around the 4th or 5th day. It is generally brief (24 to 48 h) but may develop into a severe form characterized by major hemorrhagic manifestations, a state of shock and/or the failure of one or more organs. Development into a severe form is most often signalled by one (or more) warning sign(s), such as:

- fever (temperature of greater than 39° C.) after the 5th day;
- intense abdominal pain, persistent diarrhea, uncontrollable vomiting and complete refusal of food;
- edemas and/or minor effusion;
- bleeding of mucous membranes which does not stop automatically;
- pronounced lethargy or restlessness;
- thrombocytopenia;
- signs of hemoconcentration.

In the most severe cases, the leaking of plasma can lead to deadly hypovolemic shock (Dengue Shock Syndrome: DSS) if the patient is not rapidly treated. Rare but deadly hepatic and neurological involvement is also associated with the severity of the disease. The mortality rate, which is variable according to epidemics, can reach 5% of established DHF cases. This rate can increase up to 20% without hospital care or appropriate treatments.

To simplify, these severe cases will be referred to as severe dengue, SevD in the remainder of the description, as opposed to conventional dengue, DF.

90% of cases of severe dengue occur during secondary infection with a heterologous serotype, and 10% during primary infection, generally in infants aged from 6 months to 1 year. There are several factors which influence the severity of the infection, such as the factors of the host, serotype and genotype of the virus, the order and time between successive infecting viruses, the quality and quantity of cross-reactive antibodies and the CD4/CD8 response. Studies have shown a correlation between viral load and severity of the disease. The exact causes of the occurrence of severe dengue are, however, still not known. Up until now, no specific determining factor for virulence has been demonstrated. Furthermore, since there is no vaccine against the dengue virus, the only treatments available are symptomatic treatments. Consequently, it is important to be able to monitor epidemics and to predict severe cases for appropriate hospital care.

The methods currently used to diagnose dengue do not make it possible to predict the development of severe dengue. At the very most, serological methods make it possible to distinguish between primary and secondary infections and molecular methods make it possible to detect the virus and to carry out serotyping [1, 2, 3, 4].

The present invention provides a solution to the problems presented above by means of a method which allows both early and specific detection of proteins in a blood sample making it possible to predict patients developing severe dengue. Indeed, the inventors found, surprisingly, that proteins from the host were expressed more or less abundantly (overexpressed/underexpressed) in cases of patients developing severe dengue, compared to the amount or expression thereof in cases of patients remaining with conventional dengue (that is to say not developing severe dengue) in blood samples consisting, for example, of plasma. Most particularly, they have demonstrated for the first time and completely unexpectedly that platelet factor 4 (PF4) is underexpressed in the case of patients developing severe dengue and thus constitutes a marker for predicting severe dengue.

Thus, a subject of the present invention is a method for predicting, in vitro, the probability of a patient developing severe dengue, based on a blood sample, wherein:

a) the quantity in said blood sample of at least one marker, which is platelet factor 4, is determined, b) the quantity of platelet factor 4 determined in step a) is compared with a reference quantity of said marker obtained from a group of individuals who have been diagnosed with non-severe dengue, wherein, if the quantity of platelet factor 4 determined in step a) is less than the reference quantity established in step b), it is predicted that the patient will develop severe dengue.

According to the method of the invention, it is also possible to determine, in step a), the quantity in the blood sample of at least one other marker chosen from olfactomedin 4 (OLFM4) and α2-macroglobulin (A2M) or the respective quantities of the two markers and, in step b), the quantity of the marker or of the two markers of step a) is compared with a reference quantity obtained from a group of individuals who have been diagnosed with non-severe dengue and, if the quantity of olfactomedin 4 in step a) is greater than the reference quantity established in step b) and/or the quantity of α2-macroglobulin is less than the reference quantity established in step b), it is determined that the patient will develop severe dengue.

The invention also relates to a kit for the in vitro prediction of severe dengue, comprising:
a binding partner for platelet factor 4,
a binding partner for the dengue virus NS1 protein.

The kit may also comprise a binding partner for OLFM4 and/or a binding partner for A2.

Definitions

The term "blood sample" is intended to mean whole blood, serum and plasma.

The term "group of individuals who have been diagnosed with non-severe dengue", used to determine the reference quantity of the marker of interest, is intended of course to mean that the group of individuals has not developed severe dengue. Thus, in step b) the quantity of platelet factor 4 determined in step a) is compared with a reference quantity of said marker obtained from a group of individuals who have been diagnosed with dengue without having developed severe dengue.

The term "binding partner" is intended to mean, for example, receptors, antibodies, antibody fragments, antibody analogs and any other ligand capable of binding to a protein.

The binding-partner antibodies are, for example, either polyclonal antibodies or monoclonal antibodies.

The polyclonal antibodies may be obtained by immunization of an animal with the appropriate immunogen, followed by recovery of the desired antibodies in purified form, by taking the serum of said animal, and separation of said antibodies from the other serum constituents, especially by affinity chromatography on a column to which is bound an antigen specifically recognized by the antibodies.

The monoclonal antibodies may be obtained by the hybridoma technique, the general principle of which is summarized below.

Firstly, an animal, generally a mouse, is immunized with the appropriate immunogen, and the B lymphocytes of said animal are then capable of producing antibodies against this antigen. These antibody-producing lymphocytes are then fused with "immortal" myeloma cells (murine in the example) so as to give rise to hybridomas. Using the heterogeneous mixture of cells thus obtained, a selection of the cells capable of producing a particular antibody and of multiplying indefinitely is then carried out. Each hybridoma is multiplied in the form of a clone, each resulting in the production of a monoclonal antibody of which the recognition properties with respect to the protein may be tested, for example, by ELISA, by one-dimensional or two-dimensional Western blotting, by immunofluorescence, or by means of a biosensor. The monoclonal antibodies thus selected are subsequently purified, especially according to the affinity chromatography technique described above.

The monoclonal antibodies may also be recombinant antibodies obtained by genetic engineering, using techniques well known to those skilled in the art.

The term "antibody analogs" is intended to mean biological and/or chemical compounds which have the same binding capacities as the antibodies or antibody fragments or similar binding capacities. In particular, the antibody analogs include small proteins which, like antibodies, are capable of binding to a biological target thus making it possible to detect it, to capture it or quite simply to target it within an organism or within a biological sample. The fields of application of these antibody analogs are virtually as vast as those of antibodies. By way of example, mention may be made of the Nanofitins™, which are small proteins sold by the company Affilogic.

The binding partners specific for the desired protein can be used as a capture reagent, as a detection reagent or as capture and detection reagents.

The visualization of the immunological reactions, i.e. the protein/binding partner binding, can be carried out by any means of detection, via labeling, of the binding partner.

The term "labeling" is intended to mean the binding of a label reagent capable of generating a detectable signal, i.e. a compound, a substance or a particle which can be detected by visual, fluorescent or instrumental means.

A nonlimiting list of these label reagents consists of:
metal or alloy particles, such as colloidal gold particles,
polymer particles, such as colored latex particles,
magnetic particles,
fluorescent molecules,
chemoluminescent molecules.

By way of example of immunological tests as defined above, mention may be made of "sandwich" and "competition" methods.

FIGURES

The majority of the figures illustrate the validation of the results by a quantitative ELISA assay carried out on individual samples taken from patients during the acute febrile phase of the disease, before defervescence. The patients having remained with conventional dengue are denoted DF and the patients having then developed severe dengue are denoted SevD. In all cases, the reading is carried out at an optical density (OD) of 450 nm. The results were obtained on samples with different geographical origins: Columbia and Cambodia. On the graphs obtained (GraphPad Prism software, V4.03), the median calculated is represented by a horizontal line. The box illustrates the values encompassing 50% of the individuals. The maximum and minimum values are also illustrated. The values taken into account correspond to the mean of two independent tests carried out in duplicate.

Example 1: Characterization of the Samples

15 Colombian plasma samples positive for dengue were selected, from which 8 originate from patients remaining with conventional dengue without developing severe dengue (patients/samples referred to hereinafter as DF or conventional dengue) and 7 originate from patients having then developed severe dengue (patients/samples referred to hereinafter as SevD or severe dengue). The various plasmas were grouped together, composing respectively a pool of conventional dengue DF plasma and a pool of severe dengue SevD plasma for those having developed severe dengue. All the plasmas were taken during the acute febrile phase of the disease, before the critical phase, from patients having a secondary infection. The serotypes concerned were serotypes 1, 2 and 3. All the patients having developed severe dengue were hospitalized and had signs of hemorrhaging. No comorbidity was reported [5]. All the plasmas were verified as being NS1-positive (Platelia dengue kit, Bio-rad) and the viral load was also verified by Q-RT-PCR with a commercially available kit (PrimerDesign) following supplier instructions: the mean number of viral RNA copies was estimated at $4 \times 10^6$ and $4.1 \times 10^7$ for the conventional dengue (DF) pools and severe dengue (SevD) pools, respectively. The pools composed correspond to a volume of approximately 2 ml of plasma. Before purification, the plasma mixtures were centrifuged for 5 mins at 1000×g and at 4° C. so as to remove the impurities present in the sample and to obtain clarified samples.

The plasma selection criteria are described in table 1 below. The samples were taken after appearance of symptoms.

TABLE 1

| Colombian plasma | | DF POOL | SevD POOL |
|---|---|---|---|
| General | Number | 8 | 7 |
| | Age (mean) | 26.8 | 33.7 |
| | M/F ratio | 6/2 | 3/4 |
| | Day | 3.3 | 2.7 |
| | Secondary infection | Yes | Yes |
| | NS1 | Positive | Positive |
| Serotype | DV1 | 1 | 0 |
| | DV2 | 1 | 3 |
| | DV3 | 6 | 4 |

These plasma sample pools were then purified to obtain virus-enriched fractions as described below.

Example 2: Purification of the Samples

All the steps are carried out at 4° C. The clarified samples are supplemented with 8 ml of cold pH8 PBS (PBS8), then centrifuged for 2 h at 41 000×g in an Optima L90 ultracentrifuge (Beckman). The rotor used is the SW41 rotor (Beckman). After centrifugation, the supernatant is removed and the viral pellet obtained is resuspended in 200 microliters of PBS8 then loaded onto a discontinuous gradient composed of 5 ml of 60% (w/w) sucrose in PBS8 and 5 ml of 20% (w/w) sucrose in PBS8. After renewed centrifugation for 2 h at 41 000×g, a virion-enriched ring located at the interface between the two sucrose solutions is taken off with a pipette, diluted 10 times with PBS8 and finally centrifuged one last time for 2 h at 41 000×g. The pellet obtained is resuspended in 200 microliters of PBS8.

Figure 1:
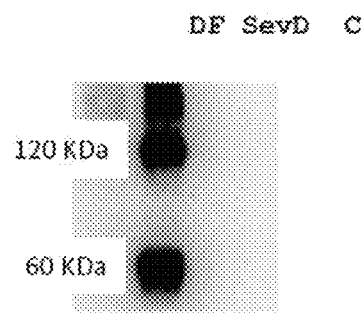
FIG. 1 illustrates the presence of virus in the fractions purified from plasma from patients but not in the control (C), demonstrated with Western blotting using a monoclonal antibody directed against the viral protein E.

This resuspension is then purified using an insoluble polyelectrolyte, Viraffinity (BioSupportGroup, USA). For this purpose, 200 microliters of an MN buffer (60 mM MES pH 6.5, 150 mM NaCl) are added to the viral suspension along with 100 microliters of Viraffinity. The mixture is incubated for 5 min at room temperature then centrifuged for 10 min at 1000×g, following supplier instructions. The supernatant is removed and the polymer pellet is rinsed 3 times with 200 microliters of MN buffer. The viral proteins are recovered by heating the polymer for 5 min/70° C. in the presence of 50 microliters of a buffer containing SDS (Novex InVitrogen) then centrifugation for 5 min at 1000×g. The presence of the virus in the final samples was verified by immunoblotting with a monoclonal antibody directed against the envelope protein of the dengue virus (E protein). As illustrated in FIG. 1, strong signals at 60 KDa and 120 KDa, corresponding respectively to the monomeric and dimeric forms of the envelope protein, are specifically detected by the monoclonal antibody in the plasma pools. On the contrary, the envelope protein was not detected on a control corresponding to a pool of healthy (non-dengue) plasma purified in the same way as has been described above.

Example 3: Identification of the Specific Proteins for Each Plasma Pool, Conventional Dengue DF and Severe Dengue SevD, by Mass Spectrometry (MS)

Method:

The viral preparations and the control sample obtained according to example 2 are deposited on a non-denaturing polyacrylamide gel and migrated until the proteins penetrate into the gel, in order to desalify the sample. The band containing the proteins is excised manually then washed three times in a buffer containing 50% acetonitrile then finally dried in 100% acetonitrile. The gel is then rehydrated in a 7% $H_2O_2$ solution before being washed again. A solution of trypsin diluted in 25 mM $NH_4HCO_3$ is then added for hydrolysis at 37° C. overnight. The peptides thus obtained are extracted by 15 minute sequential extractions with 30 microliters of 50% acetonitrile, 30 microliters of 5% formic acid and 30 microliters of 100% acetonitrile. These sequential extractions are mixed, dried under vacuum and resuspended in a solution containing 5% acetonitrile and 0.1% trifluoroacetic acid. After quantification of the samples, a defined quantity of peptides is analyzed by nano liquid chromatography coupled together with mass spectrometry (Ultimate 3000, Dionex and LTQ-Orbitrap VelosPro, Thermo Fisher Scientific). The results are acquired by virtue of the Xcalibur software (Thermo Fisher) and automatically converted by the Mascot Daemon V2.2 software (Matrix Science). Searching is then carried out on the Swissprot and Trembl databases via Mascot 2.2. Each experiment was carried out twice, independently. The proteins were identified by the EDyP Service laboratory (CEA Grenoble, France).

Results:

The viral envelope protein E was repeatedly identified in the samples containing virus. The predominantly identified peptide sequence is GWGNGCGLLFKG. This result confirms the presence of the virus in the purified fraction.

For the proteins of cellular origin, identified by proteomics on purified plasma pools, the results obtained are summarized in tables 2a and 2b. In these tables, only those proteins having a variance of less than 25% for the number of peptides found from one experiment to the other have been considered. Similarly, for the severe dengue sample, a number of peptides of greater than 2 was required. According to these criteria, 189 proteins were finally selected. These proteins are described in tables 2a and 2b below. A ratio of "number of peptides in severe dengue (SevD) sample"/"number of peptides in conventional dengue (DF) sample" (SevD/DF) could be calculated for the majority of these proteins (cf. table 2a). Some proteins were only identified in the SevD sample (cf. table 2b); in this case, the SevD/DF ratio could not be calculated.

TABLE 2a

| Accession number | Protein name | Mean number of peptides DF | Mean number of peptides SevD | SevD/DF peptides ratio |
| --- | --- | --- | --- | --- |
| P09871 | Complement C1s subcomponent (C1 esterase) | 3.5 | 14.5 | 4.14 |
| P07225 | Vitamin K-dependent protein S | 1 | 4 | 4.00 |
| P01008 | Antithrombin-III (ATIII) (Serpin C1) | 3 | 9.5 | 3.17 |
| Q16610 | Extracellular matrix protein 1 (Secretory component p85) | 1 | 3 | 3.00 |
| P27918 | Properdin (Complement factor P) | 1.5 | 4 | 2.67 |
| B4E1B2 | Serotransferrin | 11 | 29 | 2.64 |
| Q53H26 | Transferrin variant (Fragment) | 11 | 29 | 2.64 |
| B4DPQ0 | Complement C1r subcomponent | 5 | 13 | 2.60 |
| P01019 | Angiotensinogen (Serpin A8) | 1 | 2.5 | 2.50 |
| B4DDU2 | Tubulin alpha-ubiquitous chain | 2.5 | 6 | 2.40 |
| P01779 | Ig heavy chain V-III region TUR | 2.5 | 6 | 2.40 |
| P68366 | Tubulin alpha-4A chain (Alpha-tubulin 1) | 3 | 6.5 | 2.17 |
| P00734 | Prothrombin (Coagulation factor II) | 2 | 4 | 2.00 |
| P21333 | Filamin-A (Actin-binding protein 280) | 14.5 | 28.5 | 1.97 |
| P00450 | Ceruloplasmin (EC 1.16.3.1) (Ferroxidase) | 8.5 | 16.5 | 1.94 |
| E7EX29 | 14-3-3 protein zeta/delta (Fragment) | 4.5 | 8.5 | 1.89 |
| P63104 | 14-3-3 protein zeta/delta (KCIP-1) | 4.5 | 8.5 | 1.89 |
| B4E1D8 | cDNA FLJ51597, highly similar to C4b-binding protein | 10.5 | 19 | 1.81 |
| P18206 | Vinculin (Metavinculin) | 5 | 9 | 1.80 |
| P12814 | Alpha-actinin-1 (Alpha-actinin cytoskeletal isoform) | 6.5 | 11.5 | 1.77 |
| O43707 | Alpha-actinin-4 (F-actin cross-linking protein) | 6.5 | 11.5 | 1.77 |
| P06396 | Gelsolin (AGEL) (Actin-depolymerizing factor) | 3.5 | 6 | 1.71 |
| P05106 | Integrin beta-3 (Platelet membrane glycoprotein IIIa) (GPIIIa) | 5.5 | 9 | 1.64 |
| P08514 | Integrin alpha-IIb (GPIIb) (Platelet membrane glycoprotein IIb) | 12.5 | 20 | 1.60 |
| P01833 | Polymeric immunoglobulin receptor (PIgR) | 2.5 | 4 | 1.60 |
| Q9Y490 | Talin-1 | 28.5 | 43 | 1.51 |
| A2J1N9 | Rheumatoid factor RF-ET12 (Fragment) | 3 | 4.5 | 1.50 |
| Q5NV90 | V2-17 protein (Fragment) | 3 | 4.5 | 1.50 |
| P01023 | α-2-macroglobulin (Alpha-2-M) | 56.5 | 83 | 1.47 |
| A2KBC6 | Anti-Factor VIII scFv (Fragment) | 6.5 | 9.5 | 1.46 |
| P01011 | Alpha-1-antichymotrypsin (ACT) (Serpin A3) | 3.5 | 5 | 1.43 |
| P00738 | Haptoglobin | 13.5 | 19 | 1.41 |
| P02743 | Serum amyloid P-component (SAP) | 2.5 | 3.5 | 1.40 |
| P01024 | C3 and PZP-like α-2-macroglobulin domain-containing protein 1 | 60.5 | 84.5 | 1.40 |
| A8K008 | cDNA FLJ78387 | 17.5 | 24 | 1.37 |
| A2IPI5 | HRV Fab 026-VL (Fragment) | 3 | 4 | 1.33 |
| Q6UX06 | Olfactomedin 4 (OLM4) (Antiapoptotic protein GW112) | 4.5 | 6 | 1.33 |
| P03952 | Plasma kallikrein (EC 3.4.21.34) (Fletcher factor) | 1.5 | 2 | 1.33 |
| P08567 | Pleckstrin (Platelet 47 kDa protein) (p47) | 1.5 | 2 | 1.33 |
| P07996 | Thrombospondin-1 | 19.5 | 26 | 1.33 |
| P07437 | Tubulin beta chain (Tubulin beta-5 chain) | 4.5 | 6 | 1.33 |
| A2MYD4 | V2-7 protein (Fragment) | 3 | 4 | 1.33 |
| P00488 | Coagulation factor XIII A chain (EC 2.3.2.13) | 3.5 | 4.5 | 1.29 |
| Q71U36 | Tubulin alpha-1A chain (Alpha-tubulin 3) | 3.5 | 4.5 | 1.29 |
| P68363 | Tubulin alpha-1B chain (Alpha-tubulin ubiquitous) | 3.5 | 4.5 | 1.29 |
| Q9BQE3 | Tubulin alpha-1C chain (Alpha-tubulin 6) | 3.5 | 4.5 | 1.29 |
| Q9H4B7 | Tubulin beta-1 chain | 3.5 | 4.5 | 1.29 |
| Q96K68 | cDNA FLJ14473 fis, clone | 12 | 15 | 1.25 |

TABLE 2a-continued

| Accession number | Protein name | Mean number of peptides DF | Mean number of peptides SevD | SevD/DF peptides ratio |
|---|---|---|---|---|
| | MAMMA1001080 | | | |
| P08107 | Heat shock 70 kDa protein 1A/1B | 2 | 2.5 | 1.25 |
| P34931 | Heat shock 70 kDa protein 1-like | 2 | 2.5 | 1.25 |
| P11142 | Heat shock cognate 71 kDa protein | 2 | 2.5 | 1.25 |
| Q6N089 | Putative uncharacterized protein DKFZp686P15220 | 15 | 18.5 | 1.23 |
| P02675 | Fibrinogen beta chain | 11 | 13.5 | 1.23 |
| P00739 | Haptoglobin-related protein | 12 | 14.5 | 1.21 |
| Q86UX7 | Fermitin family homolog 3 (Kindlin-3) | 5 | 6 | 1.20 |
| P02751 | Fibronectin (FN) | 61.5 | 72.5 | 1.18 |
| B7ZLE5 | FN1 protein | 61.5 | 72.5 | 1.18 |
| Q6MZM7 | Putative uncharacterized protein DKFZp686O12165 | 61.5 | 72.5 | 1.18 |
| Q68CX6 | Putative uncharacterized protein DKFZp686O13149 | 61.5 | 72.5 | 1.18 |
| P68032 | Actin, alpha cardiac muscle 1 (Alpha-cardiac actin) | 8.5 | 10 | 1.18 |
| Q562R1 | Beta-actin-like protein 2 (Kappa-actin) | 8.5 | 10 | 1.18 |
| P0C0L4 | Complement C4-A (Acidic complement C4) | 52 | 61 | 1.17 |
| P0C0L5 | Complement C4-B (Basic complement C4) | 52 | 61 | 1.17 |
| B0UZ85 | Complement component 4B (Childo blood group) | 53 | 62 | 1.17 |
| Q6MZQ6 | Putative uncharacterized protein DKFZp686G11190 | 15 | 17.5 | 1.17 |
| P07477 | Trypsin-1 (EC 3.4.21.4) (Serine protease 1) | 3 | 3.5 | 1.17 |
| Q4TZM4 | Hemoglobin beta chain (Fragment) | 6.5 | 7.5 | 1.15 |
| P04004 | Vitronectin (VN) (S-protein) (V75) | 6.5 | 7.5 | 1.15 |
| B2RUT6 | Complement component 4A (Rodgers blood group) | 53.5 | 61.5 | 1.15 |
| P01031 | Complement C5 | 3.5 | 4 | 1.14 |
| Q9UL78 | Myosin-reactive immunoglobulin light chain variable region | 3.5 | 4 | 1.14 |
| Q5NV62 | V3-4 protein (Fragment) | 6 | 7 | 1.17 |
| A6H8M8 | C4A protein (Complement C4 gamma chain) | 53.5 | 61 | 1.14 |
| P02768 | Serum albumin | 51.5 | 58.5 | 1.14 |
| Q7Z351 | Putative uncharacterized protein DKFZp686N02209 | 15 | 17 | 1.13 |
| P02649 | Apolipoprotein E (Apo-E) | 4 | 4.5 | 1.13 |
| P01009 | Alpha-1-antitrypsin (Alpha-1 protease inhibitor) (Serpin A1) | 8.5 | 9.5 | 1.12 |
| Q08380 | Galectin-3-binding protein (Basement membrane autoantigen p105) | 12 | 13 | 1.08 |
| Q6N092 | Putative uncharacterized protein DKFZp686K18196 (Fragment) | 12 | 13 | 1.08 |
| P63261 | Actin, cytoplasmic 2 (Gamma-actin) | 20 | 21.5 | 1.08 |
| P02671 | Fibrinogen alpha chain | 9.5 | 10 | 1.05 |
| P60709 | Actin, cytoplasmic 1 (Beta-actin) | 19.5 | 20.5 | 1.05 |
| A2MYE1 | A30 (Fragment) | 4 | 4 | 1.00 |
| Q96SA9 | Anti-streptococcal/anti-myosin immunoglobulin kappa light chain | 3.5 | 3.5 | 1.00 |
| P06576 | ATP synthase subunit beta, mitochondrial (EC 3.6.3.14) | 2 | 2 | 1.00 |
| O43866 | CD5 antigen-like (CT-2) (IgM-associated peptide) | 15 | 15 | 1.00 |
| P12259 | Coagulation factor V (Activated protein C cofactor) | 1.5 | 1.5 | 1.00 |
| P02747 | Complement C1q subcomponent subunit C | 5.5 | 5.5 | 1.00 |
| P04196 | Histidine-rich glycoprotein (HPRG) | 1.5 | 1.5 | 1.00 |
| P01892 | HLA class I, A-2 alpha chain (MHC class I antigen A*2) | 3 | 3 | 1.00 |
| P30447 | HLA class I histocompatibility antigen, A-23 alpha chain | 3 | 3 | 1.00 |
| F6IQP2 | MHC class I antigen (Fragment) | 3 | 3 | 1.00 |
| F6IR35 | MHC class I antigen (Fragment) | 3 | 3 | 1.00 |
| A2NKM7 | NANUC-2 heavy chain (Fragment) | 3 | 3 | 1.00 |
| P26022 | Pentraxin-related protein PTX3 (Pentraxin-related protein PTX3) | 2 | 2 | 1.00 |
| P02760 | Protein AMBP | 2.5 | 2.5 | 1.00 |
| A2J1M8 | Rheumatoid factor RF-IP12 (Rheumatoid factor RF-IP13) | 3 | 3 | 1.00 |
| A2J1N0 | Rheumatoid factor RF-IP14 (Fragment) | 6 | 6 | 1.00 |
| Q9HCC1 | Single chain Fv (Fragment) | 7.5 | 7.5 | 1.00 |
| H0YLA9 | Uncharacterized protein | 2 | 2 | 1.00 |
| P02774 | Vitamin D-binding protein (DBP) (VDB) | 2 | 2 | 1.00 |
| P02647 | Apolipoprotein A-I (ApoA-I) (Apolipoprotein A1) | 11 | 10.5 | 0.95 |
| P68871 | Hemoglobin subunit beta (Beta-globin) | 8.5 | 8 | 0.94 |
| A2NYQ9 | Anti-folate binding protein (Fragment) | 7 | 6.5 | 0.93 |

TABLE 2a-continued

| Accession number | Protein name | Mean number of peptides DF | Mean number of peptides SevD | SevD/DF peptides ratio |
|---|---|---|---|---|
| A2JA14 | Anti-mucin1 heavy chain variable region (Fragment) | 6.5 | 6 | 0.92 |
| B6EDE2 | Epididymis luminal protein 180 (Fragment) | 6.5 | 6 | 0.92 |
| Q14477 | Hbbm fused globin protein (Fragment) | 6.5 | 6 | 0.92 |
| Q670S4 | Hemoglobin Lepore-Baltimore (Fragment) | 6.5 | 6 | 0.92 |
| P02042 | Hemoglobin subunit delta (Delta-globin) | 6.5 | 6 | 0.92 |
| Q9UL90 | Myosin-reactive immunoglobulin heavy chain variable region | 6.5 | 6 | 0.92 |
| A2NZ55 | Variable immnoglobulin anti-estradiol heavy chain | 6.5 | 6 | 0.92 |
| Q15485 | Ficolin-2 (37 kDa elastin-binding protein) | 5.5 | 5 | 0.91 |
| Q9UL88 | Myosin-reactive immunoglobulin heavy chain variable region | 5 | 4.5 | 0.90 |
| Q6ZVX0 | cDNA FLJ41981 fis, clone SMINT2011888 | 9.5 | 8.5 | 0.89 |
| Q7Z374 | Putative uncharacterized protein DKFZp686C02218 | 9.5 | 8.5 | 0.89 |
| Q6MZX9 | Putative uncharacterized protein DKFZp686M08189 | 9.5 | 8.5 | 0.89 |
| P02679 | Fibrinogen gamma chain | 12.5 | 11 | 0.88 |
| Q6P5S8 | antioxidant activity; very-low-density lipoprotein particle remodeling | 16 | 14 | 0.88 |
| P27105 | Erythrocyte band 7 integral membrane protein (Stomatin) | 4 | 3.5 | 0.88 |
| P69905 | Hemoglobin subunit alpha (Alpha-globin) | 4 | 3.5 | 0.88 |
| Q6GMX0 | Putative uncharacterized protein | 16 | 14 | 0.88 |
| P02792 | Ferritin light chain (Ferritin L subunit) | 3.5 | 3 | 0.86 |
| Q9UL71 | Myosin-reactive immunoglobulin heavy chain variable region | 7 | 6 | 0.86 |
| Q07954 | Prolow-density lipoprotein receptor-related protein 1 (LRP-1) | 7 | 6 | 0.86 |
| A1A508 | PRSS3 protein | 3.5 | 3 | 0.86 |
| Q6P5S3 | Putative uncharacterized protein | 7 | 6 | 0.86 |
| Q65ZC9 | Single-chain Fv (Fragment) | 7 | 6 | 0.86 |
| Q5CZ94 | Putative uncharacterized protein DKFZp781M0386 | 6.5 | 5.5 | 0.85 |
| P19823 | Inter-alpha-trypsin inhibitor heavy chain H2 (ITI-HC2) | 9.5 | 8 | 0.84 |
| Q16195 | Keratin (Fragment) | 9.5 | 8 | 0.84 |
| P30464 | HLA class I, B-15 alpha chain (MHC class I antigen B*15) | 3 | 2.5 | 0.83 |
| P03989 | HLA class I, B-27 alpha chain (MHC class I antigen B*27) | 3 | 2.5 | 0.83 |
| Q9UL83 | Myosin-reactive immunoglobulin light chain variable region | 3 | 2.5 | 0.83 |
| P35579 | Myosin-9 (Myosin heavy chain 9) | 8.5 | 7 | 0.82 |
| A0A5E4 | Putative uncharacterized protein | 8.5 | 7 | 0.82 |
| P10909 | Clusterin (Apolipoprotein J) (Apo-J) | 5.5 | 4.5 | 0.82 |
| Q5EFE6 | Anti-RhD monoclonal T125 kappa light chain | 16 | 13 | 0.81 |
| Q86TT1 | Full-length cDNA clone CS0DD006YL02 of Neuroblastoma | 28 | 22.5 | 0.80 |
| O14791 | Apolipoprotein L1 (ApoL-I) | 2.5 | 2 | 0.80 |
| A2NB45 | Cold agglutinin FS-1 L-chain (Fragment) | 2.5 | 2 | 0.80 |
| A2NB44 | Cold agglutinin FS-2 H-chain (Fragment) | 2.5 | 2 | 0.80 |
| B1N7B8 | Cryocrystalglobulin CC1 kappa light chain variable region | 2.5 | 2 | 0.80 |
| Q865X2 | Full-length cDNA clone CS0DL004YM19 of B cells | 2.5 | 2 | 0.80 |
| Q7Z3Y6 | Rearranged VH4-34 V gene segment (Fragment) | 2.5 | 2 | 0.80 |
| A0N5G5 | Rheumatoid factor D5 light chain (Fragment) | 2.5 | 2 | 0.80 |
| H0YK52 | Uncharacterized protein | 2.5 | 2 | 0.80 |
| Q14624 | Inter-alpha-trypsin inhibitor heavy chain H4 (ITI-HC4) | 16 | 12.5 | 0.78 |
| P31946 | 14-3-3 protein beta/alpha (KCIP-1) | 4.5 | 3.5 | 0.78 |
| P62258 | 14-3-3 protein epsilon (14-3-3E) | 4.5 | 3.5 | 0.78 |
| Q04917 | 14-3-3 protein eta (Protein AS1) | 4.5 | 3.5 | 0.78 |
| P61981 | 14-3-3 protein gamma (KCIP-1) | 4.5 | 3.5 | 0.78 |
| P27348 | 14-3-3 protein theta (Protein HS1) | 4.5 | 3.5 | 0.78 |
| A2NUT2 | Lambda-chain (AA −20 to 215) | 9 | 7 | 0.78 |
| P02776 | Platelet factor 4 (PF-4) | 4 | 3 | 0.75 |
| P10720 | Platelet factor 4 variant (CXCL4L1) | 4 | 3 | 0.75 |
| P02746 | Complement C1q subcomponent subunit B | 9.5 | 7 | 0.74 |
| P48740 | Mannan-binding lectin serine protease 1 (EC 3.4.21.—) | 7.5 | 5.5 | 0.73 |

TABLE 2a-continued

| Accession number | Protein name | Mean number of peptides DF | Mean number of peptides SevD | SevD/DF peptides ratio |
|---|---|---|---|---|
| Q96JD0 | Amyloid lambda 6 light chain variable region SAR (Fragment) | 9 | 6.5 | 0.72 |
| Q6GMV8 | Putative uncharacterized protein | 9 | 6.5 | 0.72 |
| Q8NEJ1 | Putative uncharacterized protein | 9 | 6.5 | 0.72 |
| A0N5G3 | Rheumatoid factor G9 light chain (Fragment) | 9 | 6.5 | 0.72 |
| P02745 | Complement C1q subcomponent subunit A | 3.5 | 2.5 | 0.71 |
| P60660 | Myosin light polypeptide 6 (MLC-3) | 3.5 | 2.5 | 0.71 |
| Q6MZU6 | Putative uncharacterized protein DKFZp686C15213 | 17.5 | 12.5 | 0.71 |
| Q6N093 | Putative uncharacterized protein DKFZp686I04196 (Fragment) | 17.5 | 12.5 | 0.71 |
| P61224 | Ras-related protein Rap-1b (GTP-binding protein smg p21B) | 3 | 2 | 0.67 |
| P19105 | Myosin regulatory light chain 12A (MLC-2B) | 4 | 2.5 | 0.63 |
| P05387 | 60S acidic ribosomal protein P2 (Renal carcinoma antigen NY-REN-44) | 2.5 | 1.5 | 0.60 |
| P19338 | Nucleolin (Protein C23) | 10 | 6 | 0.60 |
| O75636 | Ficolin-3 (Collagen/fibrinogen domain-containing lectin 3 p35) | 3.5 | 2 | 0.57 |
| F8VWA4 | Uncharacterized protein | 3.5 | 2 | 0.57 |
| B7Z539 | cDNA FLJ56954 | 8 | 4.5 | 0.56 |
| Q96CX2 | BTB/POZ domain-containing protein KCTD12 (Pfetin) | 4.5 | 2.5 | 0.56 |
| P02730 | Band 3 anion transport protein(AE 1) | 17.5 | 9.5 | 0.54 |
| P23528 | Cofilin-1 (p18) | 3 | 1.5 | 0.50 |
| P06748 | Nucleophosmin (NPM) | 3 | 1.5 | 0.50 |
| Q6N091 | Putative uncharacterized protein DKFZp686C02220 | 7 | 3.5 | 0.50 |
| Q6N041 | Putative uncharacterized protein DKFZp686O16217 (Fragment) | 7 | 3.5 | 0.50 |
| P11166 | Solute carrier family 2, facilitated glucose transporter member 1 | 2 | 1 | 0.50 |
| P04275 | von Willebrand antigen 2 | 61.5 | 28.5 | 0.46 |
| P62805 | Histone H4 | 2.5 | 1 | 0.40 |
| Q13201 | Multimerin-1 (EMILIN-4) | 11 | 4 | 0.36 |
| B7Z1F8 | cDNA FLJ53025, highly similar to Complement C4-B | 52 | 16 | 0.31 |
| P04114 | Apolipoprotein B-100 (Apo B-100) | 25 | 7.5 | 0.30 |
| Q8TCG3 | TPMsk3 (Fragment) | 5 | 1.5 | 0.30 |
| P16452 | Erythrocyte membrane protein band 4.2 (P4.2) | 5.5 | 1 | 0.18 |
| P11277 | Spectrin beta chain, erythrocyte (Beta-I spectrin) | 23 | 3 | 0.13 |
| P02549 | Spectrin alpha chain, erythrocyte (Erythroid alpha-spectrin) | 33 | 1.5 | 0.05 |

TABLE 2b

| Accession Number | Protein name | Mean number of peptides SevD |
|---|---|---|
| P00751 | Complement factor B (C3/C5 convertase) | 4.5 |
| P00752 | Complement component C8 alpha chain | 2 |
| P00753 | Peroxiredoxin-1 (Natural killer cell-enhancing factor A) | 2 |
| P00754 | Moesin (Membrane-organizing extension spike protein) | 2 |
| P00755 | Chloride intracellular channel protein 1 | 2 |
| P00756 | Ferritin heavy chain (Ferritin H subunit) | 2 |

Example 4: Confirmation Elisa

Method:

So as to confirm the mass spectrometry results, specific quantitative ELISAs were carried out in duplicate on individual plasmas. The proteins selected and tested, from those identified in tables 2a/2b, are those with a severe dengue (SevD)/conventional dengue (DF) ratio of greater than or equal to 1.33 and less than or equal to 0.75 with a mean number of peptides of greater than 1 for each sample and a potential link to dengue pathogenesis. This first screening made it possible to only assay those proteins most of interest. According to these criteria, the following proteins were selected:
  ceruloplasmin,
  protein S,
  properdin complement factor,
  antithrombin-III,
  secretory component p85,
  complement C1r protein,
  complement C1s protein,
  angiotensin,
  factor II,
  CFB,
  anti-factor VIII,
  serum amyloid P-component,
  olfactomedin 4 (OLFM4),
  thrombospondin,
  platelet factor 4 (PF4),
  complement C1q protein, moesine, and complement C8 protein.

Multimerin-1, apolipoprotein B-100 and von Willebrand factor were also assayed.

It should be noted that these proteins are predominantly elements of the coagulation pathway or the complement cascade.

These ELISAs were carried out by virtue of commercially available kits (USCN, China), following supplier instructions. Statistical analyses (Mann-Whitney test and ROC/AUC curve) were carried out by means of GraphPad Prism V4.03 software.

Each candidate marker was assayed on individual plasma samples. These samples are plasma samples taken during the acute febrile phase of the disease (viremic phase), these samples either originating from patients having remained with conventional dengue DF, without developing severe dengue, or from patients having developed severe dengue SevD. All the patients had secondary dengue. Only serotypes 1, 2 and 3 were represented (no serotype 4). These samples originated from l'Universidad Industrial de Santander (Bucaramanga, Colombia) [5] or from the Institut Pasteur in Cambodia (Phnom-Penh). The latter were part of a prospective study carried out in agreement with the local ethics committee. The characteristics of the two sampling sources are given in tables 3 and 4 below. The samples were collected after appearance of symptoms.

TABLE 3

|  | DF (n = 15) | SevD (n = 15) | P value |
|---|---|---|---|
| Mean age +− SD (years) | 29.3 +− 0.52 | 28.3 +− 0.5 | ns |
| % male | 60% | 53% | ns |
| Sampling (day) | 3.06 | 2.37 | ns |
| Mean weight +− SD (years) | 60.2 +− 8.6 | 50.3 +− 15.6 | ns |
| Total cholesterol (g/l) | 1.44 +− 5.4 | 1.29 +− 10.1 | 0.03 |
| AST (U/L) | 90.2 +− 9.75 | 142.7 +− 29.8 | 0.001 |
| ALT (U/L) | 69.7 +− 11.4 | 90.8 +− 24.5 | ns |
| Positive tourniquet test | 8/15 (60%) | 10/15 (66%) | ns |
| Viral load (copies/ml) | $4.05 \times 10^6$ +− 3.5 | $4.1 \times 10^7$ +− 5.22 | 0.006 |
| Serotype | DV2-DV3 | DV2-DV3 | — |
| Secondary dengue | Yes | Yes | — |
| Comorbidity | No | No | — |

TABLE 4

|  | DF (n = 23) | SevD (n = 26) | P value |
|---|---|---|---|
| Mean age +− SD (years) | 8.6 +− 0.38 | 7.3 +− 0.45 | ns |
| % male | 56% | 35.6% | ns |
| Sampling (day) | 2.6 | 3.2 | ns |
| Mean weight +− SD (years) | 20.48 +− 0.93 | 18.86 +− 0.98 | ns |
| Total cholesterol (mmol/l) | 3.32 +− 0.14 | 2.37 +− 0.12 | <0.0001 |
| HDL (mmol/l) | 0.82 +− 0.07 | 0.31 +− 0.02 | <0.0001 |
| Triglycerides (g/l) | 1.37 +− 0.17 | 2.8 +− 0.2 | <0.0001 |
| AST (IU/L) | 133.3 +− 23.18 | 302.5 +− 50.7 | 0.0043 |
| ALT (IU/L) | 66.9 +− 13.4 | 106.3 +− 21.2 | ns |
| Viral load (copies/ml) | $7.1 \times 10^8$ +− 6 | $2.06 \times 10^8$ +− 2 | ns |
| Positive tourniquet test | 19/23 (82%) | 18/26 (82.6%) | ns |
| HGB | 11.63 +− 0.15 | 13.3 +− 0.29 | <0.0001 |
| Hematocrit | 38.23 +− 0.57 | 41.62 +− 0.8 | 0.0013 |
| Hepatomegaly (ultrasound) | 8/12 (66%) | 16/26 (61.5%) | ns |

TABLE 4-continued

|  | DF (n = 23) | SevD (n = 26) | P value |
|---|---|---|---|
| Serotype | DV1 | DV1 | — |
| Secondary dengue | Yes | Yes | — |
| Comorbidity | No | No | — |

SD: standard deviation
ns: non-significant p value

Results:

For the majority of the ELISA-assayed markers, no difference in plasma concentration was observed between the DF and SevD plasmas, whether Colombian or Cambodian (p>0.1).

On the other hand, for two markers, the results make it possible to clearly distinguish those patients who then developed severe dengue SevD from those who remained solely with conventional dengue without developing severe dengue. The first marker is PF4 (platelet factor 4).

Figure 2:
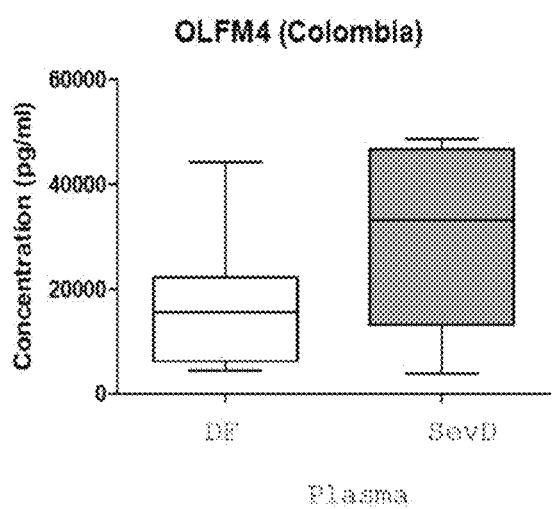
FIG. 2 illustrates the results obtained for the quantitative assaying by means of an ELISA assay of the PF4 marker on plasma samples from Colombian patients.

For the Colombian samples, a difference in plasma concentration in favor of the DF samples is observed (p<0.001) (FIG. 2). The AUC is 0.88 (95% CI: 0.7305-1).

Figure 3:
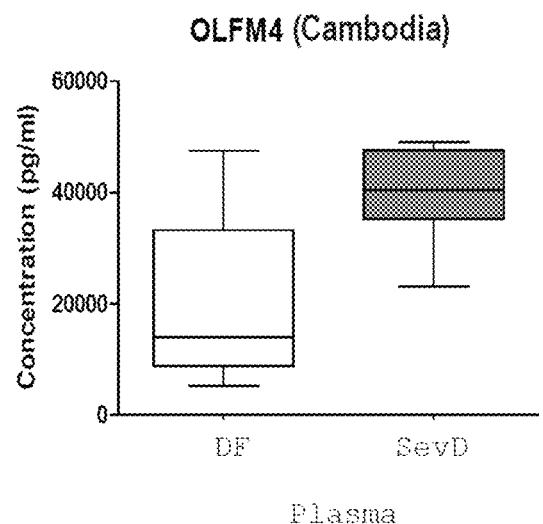
FIG. 3 illustrates the results obtained for the quantitative assaying by means of an ELISA assay of the PF4 marker on plasma samples from Cambodian patients.

This is confirmed for the Cambodian samples for which there is a significant difference in plasma concentration in favor of the DF samples (p<0.0001) (FIG. 3). The AUC is 0.94 (95% CI=0.87-1). The ROC curve made it possible to determine the best specificity for a sensitivity close to 100%. The results are summarized in table 5 below: for this marker and for a sensitivity of 95%, a specificity of close to 78% is reached.

TABLE 5

|  | For a sensitivity of: | The best specificity is: |
|---|---|---|
| PF4 | 100 | 61 |
|  | 95 | 77.9 |

The second marker is OLFM4 (olfactomedin 4)

Figure 4:
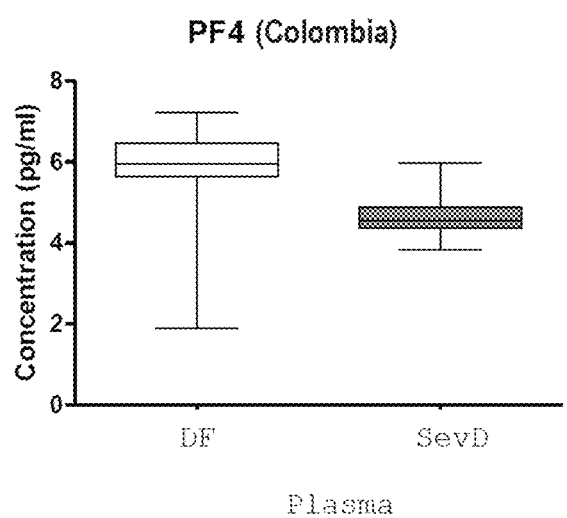
FIG. 4 illustrates the results obtained for the quantitative assaying by means of an ELISA assay of the OLFM4 marker on plasma samples from Colombian patients.

For the Colombian samples, the plasma concentration of the marker is higher in the SevD samples compared to the DF samples (p=0.07; cf. FIG. 4).

Figure 5:
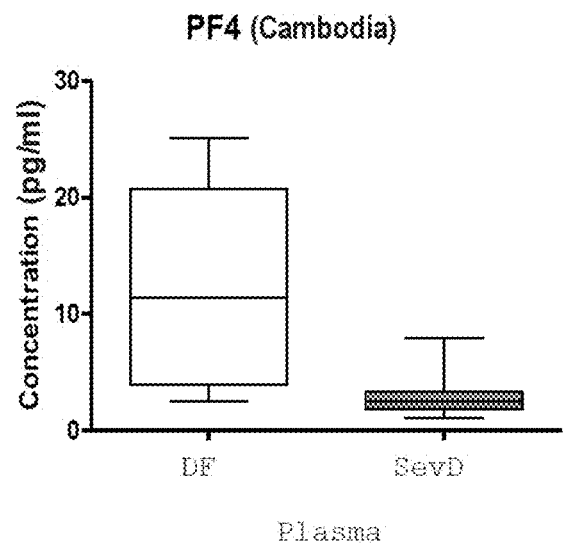
FIG. 5 illustrates the results obtained for the quantitative assaying by means of an ELISA assay of the OLFM4 marker on plasma samples from Cambodian patients.

This is confirmed on the Cambodian samples with an extremely significant difference in concentration (p<0.0003) and a median that is more than twice as high for the SevD samples compared to the DF samples (FIG. 5). The AUC is 0.858 (95% CI=0.7307-0.985). The ROC curve made it possible to determine the best specificity for a sensitivity close to 100%. The results are summarized in table 6: for this marker and for a sensitivity close to 95%, a specificity of greater than 72% is reached.

TABLE 6

|  | For a sensitivity of: | The best specificity is: |
|---|---|---|
| OLFM4 | 100 | 61 |
|  | 94.4 | 72.2 |

In parallel, another marker, α-2 macroglobulin (A2M) was identified from unpurified Cambodian plasma samples by a SILAC-type differential proteomic method (Stable Isotope Labelling by Aminoacids in cell Culture) [6]. The identification of this third marker is described in the following examples.

Example 5: Characterization of the Samples

The composition of each plasma pool or group used in this experiment is summarized in table 7. All the Cambodian plasmas selected to compose the pools were taken during the acute febrile phase of the disease, before the critical phase, from patients having a secondary infection. The serotype concerned was serotype 1. All the SevD patients were hospitalized and had signs of hemorrhaging. No comorbidity was reported. All the plasmas were verified as being NS1-positive (Platelia dengue kit, Bio-rad) and the viral load was also verified by Q-RT-PCR with a commercially available kit following supplier instructions. The pools composed correspond to a final volume of approximately 2 ml of plasma. The plasma groups are inactivated beforehand with heat (56° C./20 minutes) then preclarified by centrifugation for 5 mins at 1000×g and at 4° C., so as to remove impurities present in the sample.

TABLE 7

|  | DF (n = 6) | SevD (n = 6) |
| --- | --- | --- |
| Serotype | DV1 | DV1 |
| Secondary dengue | YES | YES |
| Age in years (mean) | 6-12 (8.6) | 6-8 (7) |
| Male/female | 2/4 | 2/4 |
| NS1 positive/virus positive | YES/YES | YES/YES |
| Mean day of sampling | 4 | 3.85 |
| Severity grade | 0-1 | 3-4 |
| Comorbidity | NO | NO |

Example 6: Differential Proteome Analysis

The method used is a semi-quantitative proteomic method of SILAC type (Stable Isotope Labelling by Aminoacids in cell Culture) [6] developed by Pronota (Ghent, Belgium) using the MASStermind™ platform and carried out on conventional dengue DF or severe dengue SevD plasma groups. Each group is composed of a mixture of 6 samples, as detailed in example 5.

These plasma mixtures have been depleted beforehand in the 14 most abundant plasma proteins by affinity chromatography. The quantity of proteins recovered in the end was obtained by a colorimetric assay based on bicinchoninic acid (BCA assay Thermo Fisher Scientific Inc., USA).

The MASStermind™ study compared each sample to a reference sample which groups together all the samples. This method provides information on the relative levels, and presence or absence, of peptides/proteins in the severe dengue SevD samples compared to the conventional dengue DF samples. The differential analysis is carried out by mixing the samples labelled with different isotopes and by analyzing, by mass spectrometry, each matched peak. The isotope label is introduced by tryptic hydrolysis which incorporates 2 $^{18}O$ atoms ("heavy" labeling) onto the C-terminal arginine of a peptide, which leads to a mass difference of 4 daltons to the same peptide labeled with $^{16}O$ ("light" labeling). The reference sample is labeled with $^{16}O$, whereas the individual samples are labeled with $^{18}O$. The MS/MS data are then submitted to the MASCOT software for identification of the peptides and proteins in each sample.

Following MS/MS analysis, more than 250 quantifiable proteins were identifiable, 10 proteins of which had at least 1 peptide found to be differential. For each protein identified, the SevD/DF ratio is calculated as the weighted mean of the coefficients of all the peptides identified for the given protein. Overall, the results showed a high degree of similarity between the two proteomes and only a few proteins were found to be expressed differentially. For three of these ten proteins, the peptides identified are systematically expressed differentially and have a mean SevD/DF ratio which deviates from 1 (cf. table 8). The three proteins identified are: α-2 macroglobulin (A2M), complement C3f and heparin cofactor 2 These proteins are predominantly elements of the coagulation pathway or the complement cascade.

TABLE 8

| Proteins | Accession number | SevD/DF ratio | 95% CI on mean of ratios |
| --- | --- | --- | --- |
| α-2 macroglobulin | A2MG_HUMAN | 0.33 | 0.25-0.44 |
| Complement C3f | CO3_HUMAN | 0.89 | 0.68-1.17 |
| Heparin cofactor 2 | HEP2_HUMAN | 2.25 | 1.71-2.95 |

Example 7: Confirmation Elisa

Method:

So as to confirm the mass spectrometry results, specific quantitative ELISAs were carried out in duplicate on individual plasmas. The proteins assayed are those identified in example 6: α-2 macroglobulin (A2M), complement C3 protein, and heparin cofactor 2.

These ELISAs were carried out by virtue of commercially available kits (USCN, China), following supplier instructions. Statistical analyses (Mann-Whitney test and ROC/AUC curve) were carried out by means of GraphPad Prism V4.03 software.

Each candidate marker was assayed on individual samples. These samples were plasma samples taken from patients during the acute febrile phase of the disease (viremic phase). Clinical follow-up of the patients showed that some finally remained with conventional dengue DF without developing severe dengue, whereas others had developed severe dengue SevD. All the patients had secondary dengue. Only serotype 1 was represented. These samples originated from the Institut Pasteur in Cambodia (Phnom-Penh) and were part of a prospective study carried out in agreement with the local ethics committee. The characteristics of the sampling source are given in table 9.

TABLE 9

|  | DF (n = 23) | SevD (n = 26) | P value |
| --- | --- | --- | --- |
| Mean age +− SD (years) | 8.6 +− 0.38 | 7.3 +− 0.45 | ns |
| % male | 56% | 35.6% | ns |
| Sampling (day) | 2.6 | 3.2 | ns |
| Mean weight +− SD (kg) | 20.48 +− 0.93 | 18.86 +− 0.98 | ns |
| Total cholesterol (mmol/l) | 3.32 +− 0.14 | 2.37 +− 0.12 | <0.0001 |
| HDL (mmol/l) | 0.82 +− 0.07 | 0.31 +− 0.02 | <0.0001 |
| Triglycerides (g/l) | 1.37 +− 0.17 | 2.8 +− 0.2 | <0.0001 |
| AST (IU/L) | 133.3 +− 23.18 | 302.5 +− 50.7 | 0.0043 |
| ALT (IU/L) | 66.9 +− 13.4 | 106.3 +− 21.2 | ns |
| Viral load (copies/ml) | $7.1\ 10^8$ +− 6 | $2.06\ 10^8$ +− 2 | ns |
| Positive tourniquet test | 19/23 (82%) | 18/26 (82.6%) | ns |
| HGB | 11.63 +− 0.15 | 13.3 +− 0.29 | <0.0001 |
| Hematocrit | 38.23 +− 0.57 | 41.62 +− 0.8 | 0.0013 |
| Hepatomegaly (ultrasound) | 8/12 (66%) | 16/26 (61.5%) | ns |

TABLE 9-continued

|  | DF (n = 23) | SevD (n = 26) | P value |
|---|---|---|---|
| Serotype | DV1 | DV1 | — |
| Secondary dengue | Yes | Yes | — |
| Comorbidity | No | No | — |

HBG: plasma hemoglobin
SD: standard deviation
ns: non-significant p value

Results:

For the majority of the ELISA-assayed markers, (complement C3f and heparin cofactor 2) no difference in plasma concentration was observed between the DF and SevD plasmas (p>0.1).

Figure 6:
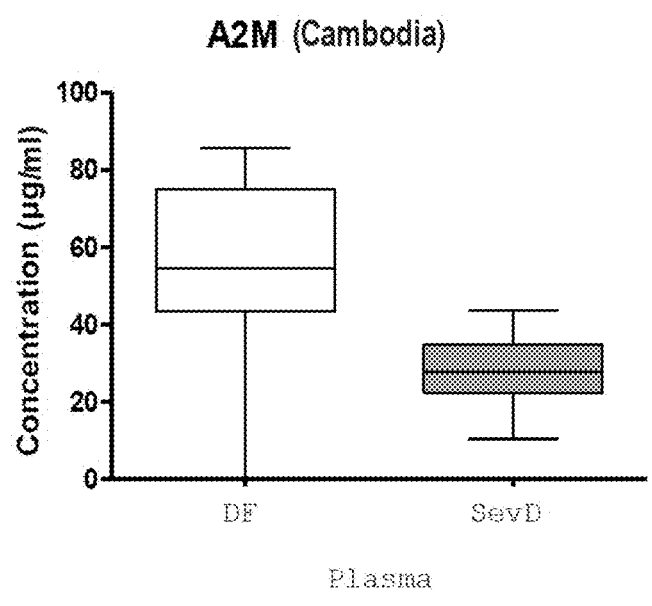
FIG. 6 illustrates the results obtained for the quantitative assaying by means of an ELISA assay of the A2M marker on plasma samples from Cambodian patients.

However, for the Cambodian samples ELISA-assayed for A2M, there was a significant difference in concentration (p<0.0004) and a median approximately twice as high for the DF samples compared to the SevD samples (FIG. 6). The AUC was 0.89 (95% CI=0.75-1).

For A2M, the ROC curve made it possible to determine the best specificity for a sensitivity close to 100%. The results are summarized in table 10: for a sensitivity close to 94%, a specificity of greater than 83% is reached.

TABLE 10

|  | For a sensitivity of: | The best specificity is: |
|---|---|---|
| A2M | 100 | 72 |
|  | 93.8 | 83.3 |

LITERATURE REFERENCES

1. S B Halstead. The lancet 2007; 370: 1644-52
2. A S Leong et al. Semin. Diagn. Pathol. 2007; 24(4):227-236
3. K. Clyde et al. J. Virol. 2006; 23: 11418-11431
4. Fields Virology, Fifth edition, Knipe D M ed., LWW
5. Villar-Centeno L A et al. Am. J. Trp. Med. Hyg. 2008; 78: 370-374 6. R. Drissi et al. FEBS J. 2013

The invention claimed is:

1. A kit for determining whether a patient will develop severe dengue, comprising:
    a binding partner for platelet factor 4; and
    a binding partner for at least one member selected from the group consisting of dengue virus NS1 protein, olfactomedin 4, and α2-macroglobulin.
2. The kit of claim 1, further comprising:
    a label reagent capable of generating a detectable signal.
3. The kit of claim 1, comprising the binding partner for dengue virus NS1 protein.
4. The kit of claim 1, comprising the binding partner for olfactomedin 4.
5. The kit of claim 1, comprising the binding partner for α2-macroglobulin.
6. The kit of claim 1, comprising the binding partners for dengue virus NS1 protein and olfactomedin 4.
7. The kit of claim 1, comprising the binding partners for dengue virus NS1 protein and α2-macroglobulin.
8. The kit of claim 1, comprising the binding partners for olfactomedin 4 and α2-macroglobulin.
9. The kit of claim 1, comprising the binding partners for dengue virus NS1 protein, olfactomedin 4, and α2-macroglobulin.

* * * * *